United States Patent [19]
Schlosser et al.

[11] Patent Number: 5,350,366
[45] Date of Patent: * Sep. 27, 1994

[54] STORAGE DEVICE WITH POSITIVE DISPLACEMENT DISPENSER BY MEANS OF EGRESS THROUGH A PIERCED SEPTEM

[75] Inventors: Mark S. Schlosser, Seattle, Wash.; Lionel S. Goldring, Irvine, Calif.

[73] Assignee: SpaceLabs Medical, Inc., Redmond, Wash.

[*] Notice: The portion of the term of this patent subsequent to May 4, 2010 has been disclaimed.

[21] Appl. No.: 992,068

[22] Filed: Dec. 17, 1992

Related U.S. Application Data

[63] Continuation of Ser. No. 535,903, Jun. 11, 1990, Pat. No. 5,207,654.

[51] Int. Cl.⁵ .............................................. A61B 5/00
[52] U.S. Cl. .................................. 604/203; 604/200; 604/201; 604/218; 604/231
[58] Field of Search ................. 604/203, 38, 143, 194, 604/36, 164, 233, 403, 218, 231, 236, 200, 201

[56] References Cited

U.S. PATENT DOCUMENTS

| | | | |
|---|---|---|---|
| 3,534,735 | 10/1970 | Sly | 604/231 |
| 4,020,831 | 5/1977 | Adler | 604/231 X |
| 4,037,464 | 7/1977 | Wenander | 604/231 |
| 4,191,225 | 3/1980 | Ogle | 604/231 X |
| 4,259,956 | 4/1981 | Ogle | 604/231 X |
| 4,390,016 | 6/1983 | Riess | 604/194 X |
| 4,648,532 | 3/1987 | Green | 604/200 X |
| 4,684,366 | 8/1987 | Denny et al. | 604/130 |
| 4,828,540 | 5/1989 | Walter | 604/164 |
| 4,976,966 | 12/1990 | Theeuwes et al. | 604/892.1 |
| 4,982,740 | 1/1991 | Broden | 604/415 X |

*Primary Examiner*—C. Fred Rosenbaum
*Assistant Examiner*—N. Kent Gring
*Attorney, Agent, or Firm*—Seed and Berry

[57] ABSTRACT

A positive displacement ampule for storing a fluid therein and dispensing the fluid therefrom. The ampule includes an elongate vessel for storing the fluid having a large diameter base portion at one end thereof joined to a small diameter stem portion at the other end thereof, a piston disposed in the vessel at the base end thereof for forcing the fluid from the vessel, a fracture probe for fracturing the base end of the vessel and a needle for inserting into the fractured base end of the vessel and for piercing the piston such that one end of the needle protrudes outwardly from the vessel and the other end of the needle communicates with the fluid in the vessel. In this manner, the fluid is pumped from the vessel through the needle by pushing the piston in the direction of the fluid. The positive displacement ampule is manufactured by providing the elongate vessel with the stem end of the vessel being open and the base end of the vessel being closed, injecting a monomer liquid into the vessel through the open stem end thereof, polymerizing the liquid so as to convert the liquid to a solid designed to function as a piston, injecting the fluid into the vessel through the open stem end thereof in such a manner as to maintain the fluid between the piston and the stem end and sealing the stem end of the vessel.

21 Claims, 2 Drawing Sheets

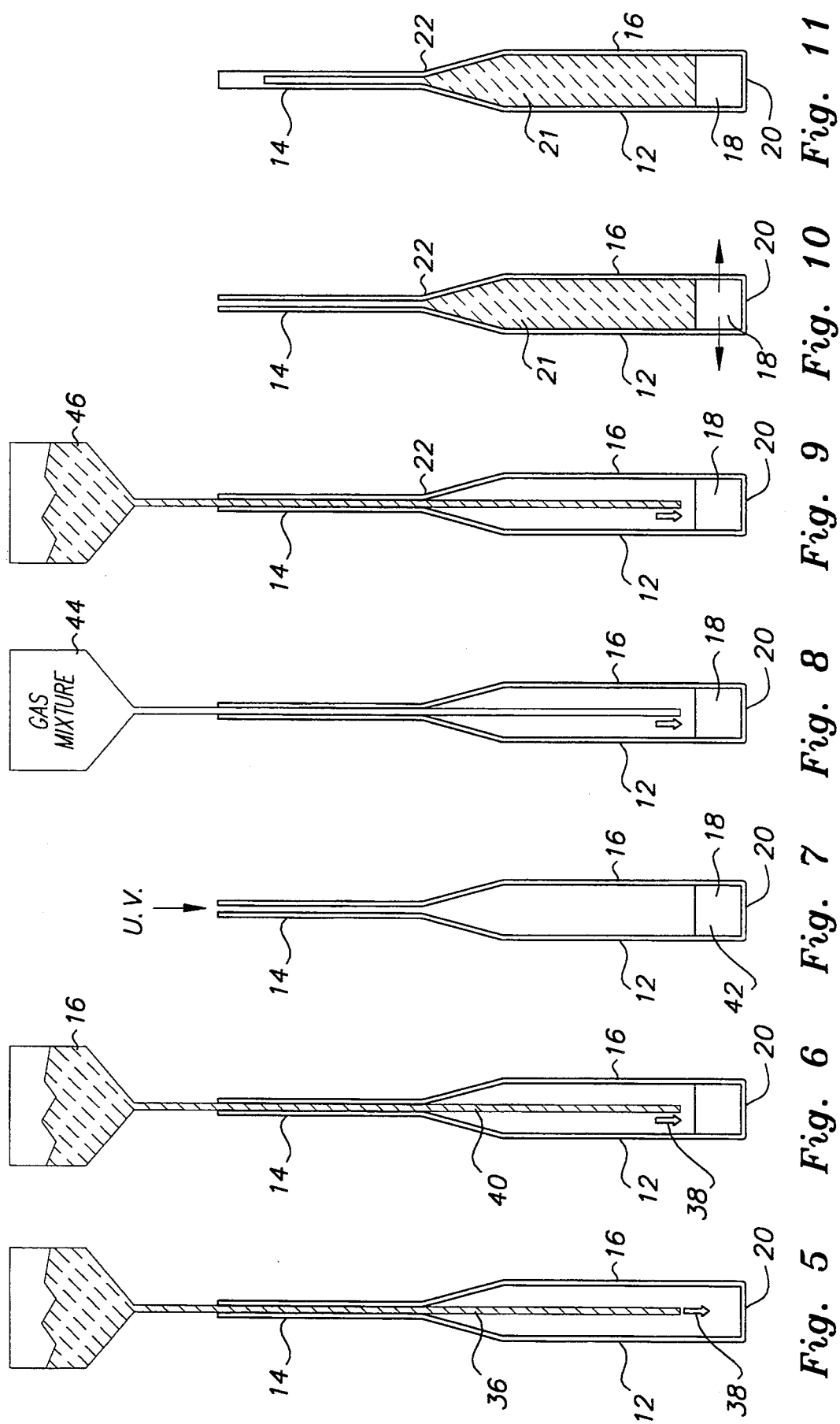

STORAGE DEVICE WITH POSITIVE DISPLACEMENT DISPENSER BY MEANS OF EGRESS THROUGH A PIERCED SEPTEM

This application is a continuation of U.S. application Ser. No. 07/535,903, filed Jun. 11, 1990, now U.S. Pat. No. 5,207,654.

TECHNICAL FIELD

This invention relates to a storage device, and more particularly, to a storage device having a positive displacement dispenser for dispensing fluid therefrom.

BACKGROUND OF THE INVENTION

There are three types of ampules that are presently known: a pressurized ampule, an evacuated ampule and a non-pressurized ampule. The pressurized ampule contains fluid or powder which is at a pressure greater than atmospheric pressure such that the fluid or powder is propelled from the ampule by breaking the tip of the ampule. This type of ampule is manufactured by introducing the fluid or powder into the opened tip end of the ampule in a pressurized atmosphere and thereafter sealing the ampule.

The evacuated ampule is primarily designed for conducting chemical analyses of water. The evacuated ampule contains a fluid at a pressure that is less than atmospheric pressure. The analysis is conducted by breaking the tip of the ampule while dispersed in the water being analyzed. Due to the low pressure in the ampule relative to the environment, the water is drawn into the ampule and mixes with the analyzing fluid or powder. The water is analyzed by observing the change in color of the mixed fluid.

The non-pressurized ampule includes stem portions at opposite ends and is filled with a fluid, such as a medicine, at atmospheric pressure. To dispense the fluid, both stems are broken and the fluid is drained from the ampule.

There are no known ampules having positive displacement capabilities which permit the user to pump the fluid contained in the ampule therefrom. Further, there are no known positive displacement devices which store fluids with gases trapped in predictable volume regions.

SUMMARY OF THE INVENTION

The present invention resides in a positive displacement ampule which allows the user to pump the fluid therefrom. The positive displacement ampule comprises an elongate vessel for storing a fluid therein having a large diameter base portion at one end thereof joined to a small diameter stem portion at the other end thereof, a piston disposed in the vessel at the base end thereof for forcing the fluid from the vessel, a fracture probe for fracturing the base end of the vessel and a needle for inserting into the fractured base end of the vessel and for piercing the piston such that one end of the needle protrudes outwardly from the vessel and the other end of the needle communicates with the fluid. In this manner the fluid is pumped from the vessel through the needle by pushing the piston in the direction of the fluid. The base of the vessel has a weakened area which permits the fracturing thereof by conventional means.

The positive displacement ampule is manufactured by manufacturing the elongate vessel with the stem end of the vessel being open and the base end of the vessel being closed, injecting a monomer liquid into the vessel through the open stem end thereof, polymerizing the liquid so as to convert the liquid to a solid, the solid being designed to function as a piston, injecting the fluid into the vessel through the open stem end thereof in such a manner as to maintain the fluid between the piston and the stem and sealing the stem end of the vessel.

BRIEF DESCRIPTION OF THE DRAWINGS

FIGS. 5 through 11 are elevational views showing the method of manufacturing the ampule according to the present invention.

DETAILED DESCRIPTION OF THE INVENTION

Figure 1:
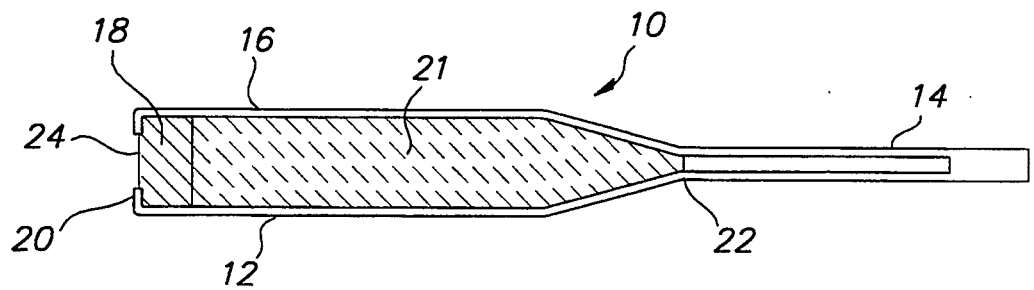
FIG. 1 is an elevational view of the positive displacement ampule according to the present invention.

Referring to FIG. 1, the positive displacement ampule 10 is an elongate vessel 12 having a small diameter stem 14 at one end thereof joined to a relatively large diameter portion 16 at the other end thereof. A cylindrical piston 18 is disposed at the base 20 of the large diameter portion with fluid 21 being contained between the piston 18 and the bottom 22 of the stem 14.

Figure 2:
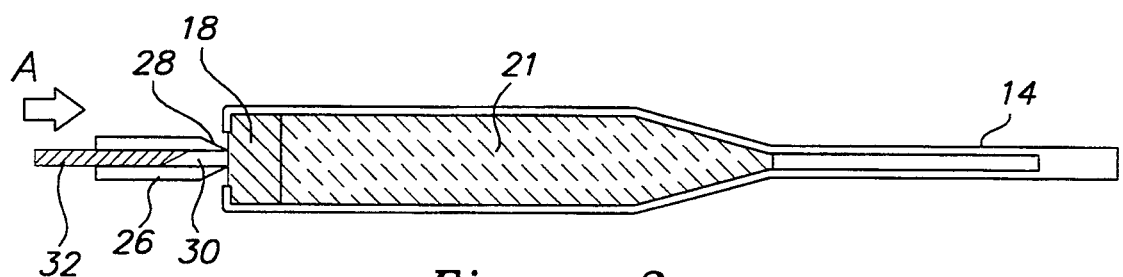
FIGS. 2 through 4 are elevational views showing the method by which the fluid in the ampule is withdrawn therefrom.

The base 20 has a weakened area 24 at the central portion thereof such that the user can fracture that portion of the base with a probe 26 illustrated in FIG. 2. The weakened area 24 can be formed by, for instance, reducing the thickness of the base of the vessel, scoring a circle in the base or providing a ceramic piece in the base. According to the preferred embodiment of the invention, the vessel 12 is made of glass and the base 20 has a plastic coating adhered to the exterior thereof. In this manner, when the base 20 is fractured the glass shards shards are retained by the coating. As illustrated in FIG. 2, the probe 26 has a pointed end 28 for fracturing the base 20 and has a bore 30 extending axially therethrough for slidably receiving a needle 32.

Figure 3:
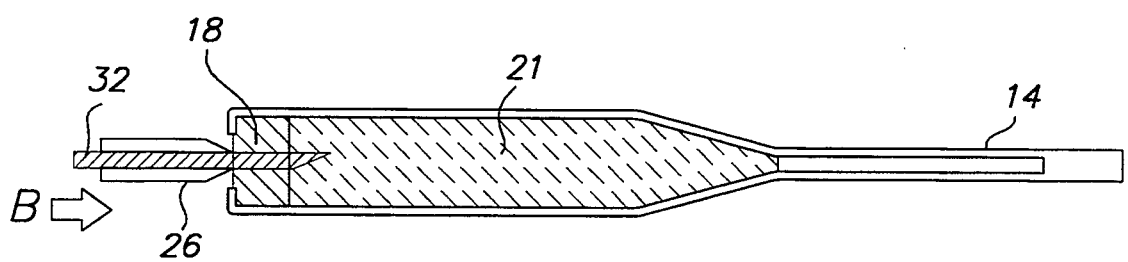
Figure 4:
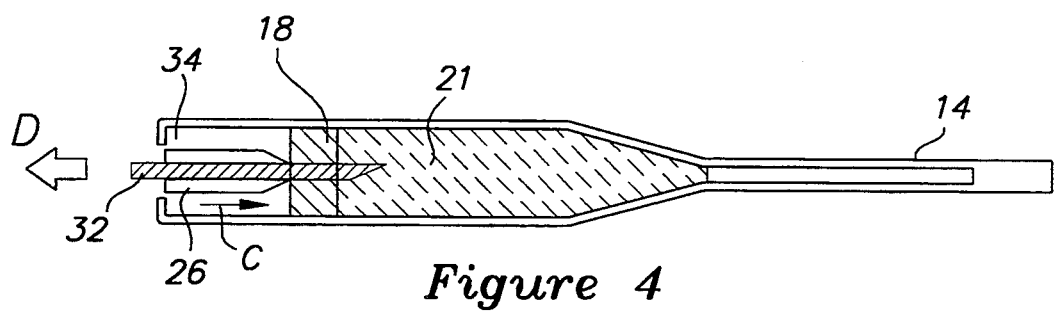

FIGS. 2 through 4 illustrate the manner in which the fluid 21 is withdrawn from the vessel 12. Referring to FIG. 2, as noted above, the base 20 of the vessel 12 is fractured by pushing the probe 26 in the direction of arrow A against the base with the necessary force. Since the base is coated with plastic, the glass shards resulting from the fracturing of the base are retained by the base. After the base 20 has been fractured, the needle 32 is pushed in the direction of arrow B illustrated in FIG. 3 to thereby pierce the piston 18 such that the needle extends into the interior of the vessel so as to communicate with the fluid 21. Thereafter, as shown in FIG. 4, both the probe 26 and the needle 32 are moved in the direction of arrow C causing the fluid to pumped through the needle and ejected from the vessel as illustrated by arrow D. The glass shards are forced into the area 34 disposed between the base 20 of the vessel 12 and the piston 18 such that they do not contaminate the ejected fluid.

Accordingly, as can be seen from the foregoing, the fluid in the vessel can be withdrawn without the necessity of fracturing the vessel in two places as in the conventional ampule discussed above. Rather, only one end of the vessel need be fractured.

FIGS. 5 through 11 illustrate the method by which the ampule 10 is manufactured. Referring to FIG. 5, initially, the vessel 12 is open at the top of the stem 14 and closed at the base 20 of the large diameter portion 16. A needle 36 is inserted into the opening and a coating agent 38 applied to the interior of the base 20. The coating agent is designed to insure that the piston liquid that is subsequently injected and polymerized does not stick to the interior of the vessel 12. After coating the base, another needle 40 is inserted through the opening and a monomer 42 containing a polymerizing agent in the form of a liquid is injected into the vessel as shown in FIG. 6. An important characteristic of the polymerizeable monomer is that, once polymerized, it expands when exposed to an aqueous solution (i.e., it is water-swellable). The specific monomer utilized is in the HEMA family and has the chemical name POLYHYDROXYETHYLMETHACRYLATE. An example of a polymerizing agent is BENZYL PEROXIDE (which is polymerized by heat) or 2,2,DIETHOXY ACETALPHENON (which is polymerized by ultraviolet light).

As illustrated in FIG. 7, the monomer liquid 42 is polymerized by exposing the liquid to ultraviolet light or, alternatively, to heat. By polymerizing the liquid, the cylindrical piston 18 is formed which is utilized to force the fluid in the vessel therefrom, as described above.

If it is important to maintain the gas concentration of the fluid in the vessel after the fluid has been polymerized, the vessel 12 may be filled with a tonometered gas mixture 44 and, thereafter, a tonometered calibrant fluid 46, as illustrated in FIGS. 8 and 9, respectively. The calibrant fluid 46 contains a known mount of carbon dioxide, oxygen and nitrogen in terms of partial pressure. This is important because when analyzing the oxygen and carbon dioxide content of blood a flow cell must be calibrated by passing a calibrant fluid having a known mount of carbon dioxide and oxygen into the flow cell. In order to prevent the calibrant fluid from releasing any of its gases and to thereby maintain the proper ratio of gases in the calibrant fluid when injecting the fluid into the vessel, it is recommended that the vessel be filed with a gas mixture having the same percentage of gases as the calibrant fluid. Accordingly, as noted above, a gas mixture 44 having a known percentage of gases, which are correspondingly present in the calibrant fluid 46, is injected into the vessel 12 prior to the injection of the calibrant fluid 46.

Subsequent thereto, as noted above, the calibrant fluid 46 is injected utilizing a needle, as illustrated in FIG. 9, such that the fluid extends up to the bottom 22 of the stem 14. At this time, the piston 18 swells sufficiently to press firmly against the interior wall of the vessel to thereby provide an adequate piston seal, as shown in FIG. 10. Specifically, the piston seals the fluid 21 in the vessel 12 such that when the weakened central area 24 of the base 20 is fractured the fluid 21 does not leak past the piston 18 and from the vessel 12. After the fluid has been injected into the vessel, the top of the stem 14 is sealed, as shown in FIG. 11.

While the above description describes the manner in which a monomer liquid is injected into the vessel and thereafter polymerized to form the piston, it is of course understood that the invention is not intended to be limited to this embodiment. Rather, any liquid (i.e., any viscous substance) that can be converted to a solid may be used to form the piston. For instance, an epoxy liquid could be injected into the vessel and thereafter converted to a solid by curing it. Moreover, while the above embodiment is directed towards filling the vessel with a calibrant fluid, it should be understood that any appropriate fluid could be stored in the vessel, such as a wash fluid. Thus, the step of injecting a tonometered gas mixture is not always required.

The vessel is capable of being filled to greater than 90% of its volume. Moreover, the stem design insures that all of the gases in the vessel are trapped in the stem 14 of the vessel, and therefore, do not mix with the fluid. In particular, the inner diameter of the stem is designed to be less than 1 mm such that the stems act as a capillary tube. In this manner, the surface tension of the fluid acts to prevent the fluid from mixing with the gases. Thus, according to the invention, the fluid can be pumped from the ampule with the ampule disposed in any orientation without effecting the position of the gases in the vessel, as discussed above. Moreover, the pump arrangement allows the fluid to be pumped from the ampule at a specific rate. Of course, it is understood that the vessel 12 need not include the stem 14 if it is not important to prevent the mixing of the fluid and the gases.

When the fluid is withdrawn from the vessel in the manner described above, an air bubble forms at the leading edge of the flow to thereby form a negative fluid meniscus. The leading edge of the negative fluid meniscus serves to scrape previous fluids from the walls of the path, such as in a flow cell, so as to prevent the previous fluids from mixing with the present fluid thereby preventing what is commonly referred to as "carry-over."

The vessel can be made out of a gas impermeable material such as glass so as to insure that the gases in the fluid do not permeate the vessel. Alternatively, the vessel can be made out of gas permeable material such as plastic if maintaining the gas concentration in the fluid is not important.

We claim:

1. A fluid storage system, comprising:
   a vessel for storing a fluid therein;
   sealing means disposed in said vessel;
   a fluid contained in said vessel, said fluid being separated by said sealing means from at least a portion of the wall of said vessel;
   access means for passing through a portion of the wall of said vessel where said sealing means separates said fluid from the wall of said vessel, said access means then passing through said sealing means such that one end of said access means communicates with said fluid and the other end of said access means extends outwardly from said vessel; and
   means for causing said fluid to flow from said vessel through said access means.

2. The fluid storage system of claim 1 wherein said access means comprise:
   probe means for passing through a portion of the wall of said vessel where said sealing means separates said fluid from the wall of said vessel; and
   penetration means insertable through the portion of the wall of said vessel through which said probe means has passed, said penetration means then passing through said sealing means such that one end of said penetration means communicates with said fluid and the other end of said penetration means extends outwardly from said vessel.

3. The fluid storage system of claim 2 wherein said penetration means is a needle having a hollow bore.

4. The fluid storage system of claim 3 wherein said sealing means is a piston slideably mounted in said vessel through which said needle extends when said needle has pierced said sealing means.

5. The fluid storage system of claim 4 wherein said means for causing said fluid to flow from said vessel includes an actuator for forcing said piston into said vessel thereby displacing fluid from said vessel through said needle.

6. The fluid storage system of claim 3 wherein said probe means is a rod having a needle receiving bore disposed therein, and wherein said needle is slideably disposed in said bore so that said rod may be used to penetrate a wall of said vessel, thereby allowing said needle to puncture said sealing means through the area of said wall that has been penetrated by said rod.

7. The fluid storage system of claim 1 wherein said vessel is an elongated container having a sidewall and at least one end wall, and wherein the portion of the wall of said vessel through which said access means passes is in said end wall of said container.

8. The fluid storage system of claim 7 wherein said vessel is fabricated from glass, and wherein said end wall of said vessel is made relatively weak in the portion of the wall of said vessel through which said access means passes thereby better allowing said access means to pass through the wall of said vessel.

9. The fluid storage system of claim 1 wherein said fluid is a liquid.

10. An fluid storage system, comprising:
   a vessel for storing a fluid therein;
   a seal disposed in said vessel;
   a fluid contained in said vessel, said fluid being separated by said seal from at least a portion of the wall of said vessel;
   an access device adapted to pass through a portion of the wall of said vessel where said seal separates said fluid from the wall of said vessel; said access device being adapted to then passing through said seal such that one end of said access device communicates with said fluid and the other end of said access extends outwardly from said vessel; and
   a fluid conveyor for causing said fluid to flow from said vessel through said penetrator.

11. The fluid storage system of claim 10 wherein said access device comprises:
   a probe adapted to pass through a portion of the wall of said vessel where said seal separates said fluid from the wall of said vessel; and
   a penetrator insertable through a portion of the wall of said vessel through which said probe is adapted to pass after said probe has passed through the wall of said vessel, said penetrator adapted to then pass through said seal such that one end of said penetrator communicates with said fluid and the other end of said penetrator extends outwardly from said vessel;

12. The fluid storage system of claim 11 wherein said penetrator is a needle having a hollow bore.

13. The fluid storage system of claim 12 wherein said seal is a piston slideably mounted in said vessel through which said needle extends when said needle has pierced said seal.

14. The fluid storage system of claim 13 wherein said fluid conveyor includes an actuator for forcing said piston into said vessel, thereby displacing fluid from said vessel through said needle.

15. The fluid storage system of claim 12 wherein said probe is a rod having a needle receiving bore disposed therein, and wherein said needle is slideably disposed in said bore so that said rod may be used to penetrate a wall of said vessel, thereby allowing said needle to puncture said seal through the area of said wall that has been penetrated by said rod.

16. The fluid storage system of claim 10 wherein said vessel is an elongated container having a sidewall and at least one end wall, and wherein the portion of the wall of said vessel through which said access device passes is in said end wall of said container.

17. The fluid storage system of claim 16 wherein said vessel is fabricated from glass, and wherein said end wall of said vessel is made relatively weak in the portion of the wall of said vessel through which said access device passes thereby better allowing said access device to pass through the wall of said vessel.

18. The fluid storage system of claim 10 wherein said fluid is a liquid.

19. A method of removing a fluid from a vessel having a seal disposed in said vessel, a fluid contained in said vessel, and a seal separating said fluid from a portion of the wall of said vessel; said method comprising:
   penetrating a portion of a wall of said vessel in an area where said seal separates said fluid from the wall of said vessel;
   penetrating said seal after entering said vessel in an area of said wall has been penetrated; and
   withdrawing said fluid from said vessel through the penetrated areas of said seal and said wall.

20. The method of claim 19 wherein said seal is a piston slideably disposed in said vessel, wherein said step of penetrating said seal is accomplished by penetrating said piston with a needle, and wherein said step of withdrawing said fluid from said vessel is accomplished by forcing said piston into said vessel, thereby displacing said fluid from said vessel through said needle.

21. The method of claim 20 wherein said seal is a piston slideably disposed in said vessel, and wherein both of said penetrating steps are accomplished by:
   providing a probe having an axial bore, and a needle slideably mounted in said bore;
   advancing said probe through an area of said wall of said vessel thereby penetrating said wall;
   advancing said needle relative to said probe thereby causing said needle to pierce said piston; and
   further advancing said probe and needle into said vessel so that said probe forces said piston into said vessel, thereby displacing said fluid from said vessel.

* * * * *

UNITED STATES PATENT AND TRADEMARK OFFICE
CERTIFICATE OF CORRECTION

PATENT NO. : 5,350,366

DATED : September 27, 1994

INVENTOR(S) : Mark S. Schlosser and Lionel S. Goldring

It is certified that error appears in the above-identified patent and that said Letters Patent is hereby corrected as shown below:

On the title page, within the patent title, please delete "SEPTEM" and substitute therefor --SEPTUM--.

In column 5, claim 10, line 31, please delete "An" and substitute therefor --A--.

In column 5, claim 10, line 39, after "vessel" and before "said", please delete ";" and substitute therefor --,--.

In column 5, claim 10, line 40, please delete "passing" and substitute therefor --pass--.

In column 5, claim 10, lines 41 and 42, after "access" and before "extends", please insert --device- In column 5, claim 10, line 45, please delete "penetrator" and substitute therefor --access device--

In column 6, claim 19, line 37, after "wall" and before "has", please insert --that--.

Signed and Sealed this

Fourth Day of April, 1995

*Attest:*

BRUCE LEHMAN

*Attesting Officer*     *Commissioner of Patents and Trademarks*